United States Patent [19]

Bowman et al.

[11] Patent Number: 5,073,635
[45] Date of Patent: Dec. 17, 1991

[54] PROCESS OF PREPARING LINEARLY-EXTENDED POLYALKYLENEPOLYAMINES EMPLOYING METAL SILICATE CATALYSTS

[75] Inventors: Robert G. Bowman; David C. Molzahn; George E. Hartwell, all of Midland, Mich.

[73] Assignee: The Dow Chemical Company, Midland, Mich.

[21] Appl. No.: 542,489

[22] Filed: Jun. 22, 1990

[51] Int. Cl.$^5$ .................. C07D 295/00; C07C 209/00
[52] U.S. Cl. ..................... 544/401; 544/357; 544/382; 544/383; 544/402; 564/479; 564/480
[58] Field of Search ............... 544/382, 383, 401, 402, 544/357; 564/479, 480

[56] References Cited

U.S. PATENT DOCUMENTS

| | | | |
|---|---|---|---|
| 2,113,241 | 4/1938 | Punnett | 260/127 |
| 3,231,616 | 1/1966 | Jones | 260/581 |
| 3,714,259 | 1/1973 | Lichtenwalter et al. | 260/583 P |
| 3,793,397 | 2/1974 | Lichtenwalter | 260/288 SY |
| 3,862,262 | 1/1975 | Hendrick et al. | 260/857 D |
| 4,014,933 | 3/1977 | Boettger et al. | 260/563 R |
| 4,049,657 | 9/1977 | Brennan et al. | 260/268 SY |
| 4,217,240 | 8/1980 | Bergna | 252/313 S |
| 4,463,193 | 7/1984 | Johnson et al. | 564/479 |
| 4,495,369 | 1/1985 | Werner et al. | 564/480 |
| 4,524,143 | 6/1985 | Vanderpool | 502/208 |
| 4,540,822 | 9/1985 | Vanderpool | 564/479 |
| 4,547,591 | 10/1985 | Brennan et al. | 564/479 |
| 4,550,209 | 10/1985 | Unvert et al. | 564/479 |
| 4,555,582 | 11/1985 | Vanderpool | 564/478 |
| 4,578,517 | 3/1986 | Johnson et al. | 564/479 |
| 4,578,518 | 3/1986 | Vanderpool et al. | 564/479 |
| 4,578,519 | 3/1986 | Larken et al. | 564/479 |
| 4,582,904 | 4/1986 | Wells et al. | 544/178 |
| 4,584,406 | 4/1986 | Vanderpool et al. | 564/479 |
| 4,588,842 | 5/1986 | Vanderpool | 564/479 |
| 4,613,705 | 9/1986 | Hargis | 564/409 |
| 4,617,418 | 10/1986 | Ford et al. | 564/479 |
| 4,827,037 | 5/1989 | Doumaux, Jr. | 564/478 |
| 4,888,425 | 12/1989 | Herdle | 544/402 |
| 4,922,024 | 5/1990 | Bowman et al. | 544/402 |
| 4,973,692 | 11/1990 | Burgess et al. | 544/402 |
| 4,977,266 | 12/1990 | Burgess et al. | 544/402 |

FOREIGN PATENT DOCUMENTS

| | | |
|---|---|---|
| 0256516 | 2/1988 | European Pat. Off. |
| 48-96475 | 12/1973 | Japan |
| 55-38329 | 3/1980 | Japan |
| 58-35179 | 3/1983 | Japan |
| 2147896 | 5/1985 | United Kingdom |

Primary Examiner—Cecilia Shen

[57] ABSTRACT

A process of preparing linearly-extended polyalkylenepolyamines, such as linear and branched polyethylenepolyamines, comprising contacting a difunctional aliphatic alcohol, such as monoethanolamine, with a reactant aliphatic amine, such as ethylenediamine, in the presence of a metal silicate catalyst wherein the metal is selected from Groups IIIB, IVB, VB and the lanthanide rare earth metals. Reactions of piperazines with alkanolamines to yield alcohol-extended and/or amine-extended piperazines are included in the process of this invention.

34 Claims, No Drawings

PROCESS OF PREPARING LINEARLY-EXTENDED POLYALKYLENEPOLYAMINES EMPLOYING METAL SILICATE CATALYSTS

BACKGROUND OF THE INVENTION

This invention relates to a process for preparing linearly-extended polyalkylenepolyamines, such as diethylenetriamine and linear and branched triethylenetetramines. Linearly-extended polyalkylenepolyamines also include for the purpose of this invention alcohol-extended piperazines, such as N-(2-hydroxyethyl)piperazine, and amine-extended piperazines, such as N-(2-aminoethyl)piperazine.

Linearly-extended polyalkylenepolyamines find utility as dispersants, surfactants, chelants, catalysts, curing agents, and extenders in polyurethanes. In addition, linearly-extended polyalkylenepolyamines are useful starting materials or intermediates in the preparation of pesticides, veterinary antihelminthic pharmaceuticals, and high temperature lubricating oils.

It is known that non-cyclic polyalkylenepolyamines can be prepared by the reaction of an alkyl halide with ammonia or an amine. The product is a polyalkylenepolyamine hydrohalide salt, which must be neutralized with base in order to recover the valuable polyalkylenepolyamine product. The neutralization produces a waste stream of metal salt, which must be removed. Moreover, the process produces considerable amounts of undesirable cyclic compounds.

It is known that salt-free linear polyethylenepolyamines can be prepared directly by reacting an ethanolamine with an ethyleneamine in the presence of hydrogen and a hydrogenation catalyst. For example, U.S. Pat. No. 3,714,259 discloses such a process with preferred catalysts derived from the oxides of chromium, copper, nickel, and cobalt. This process produces substantial quantities of undesirable cyclic products, such as piperazine. Moreover, this type of catalyst requires a large quantity of hydrogen to maintain the catalytic activity.

It is also known that alcohols can be directly aminated in a less reductive environment. For example, U.S. Pat. No. 4,524,143 and U.S. Pat. No. 4,555,582 teach the preparation of predominantly linear polyethylenepolyamines comprising reacting ethylenediamine with monoethanolamine in the presence of a catalyst of zirconium silicate having phosphorus deposited thereon. Disadvantageously, this catalyst contains phosphorus compounds which can leach into the reaction mixture, react with amines, and plug the reactor.

European Patent Application 0 256 516 teaches the preparation of non-cyclic polyalkylenepolyamines comprising reacting an alkylenediamine, such as ethylenediamine, with an alkanolamine, such as monoethanolamine, in the presence of a catalyst containing niobium, specifically niobium oxides, niobium halides, and niobium alkoxides Suitable reactants for this process also include piperazine, hydroxyalkylpiperazines and aminoalkylpiperazines.

U.S. Pat. No. 4,827,037 teaches a process of preparing polyalkylenepolyamines by reacting an alkyleneamine with an alkanolamine in the presence of a catalytically effective amount of a Group IIIB or IVB metal acid phosphate, such as lanthanum acid phosphate or zirconium phosphate, or a Group IVB sulfate or nitrate, such as zirconium sulfate or zirconium nitrate. The Group IIIB acid phosphates are taught to include the dihydrogen phosphates of scandium, cerium, samarium, europium, thulium, erbium, ytterbium, yttrium, lutetium, thorium, neodymium, praseodymium, dysprosium and gadolinium. U.S. Pat. No. 4,463,193, U.S. Pat. No. 4,578,517, and U.S. Pat. No. 4,617,418 teach along similar lines. Disadvantageously, some of these catalysts may disintegrate in the presence of water.

U.K. Patent Application 2,147,896A discloses a process of forming diethylenetriamine by reacting monoethanolamine with ammonia in the presence of ethylenediamine and a metal phosphate catalyst wherein the metal is chosen from Groups IIIB, IVB, VB and IIIA of the Periodic Table among others. Thus, lanthanum, yttrium, zirconium, titanium, vanadium, and niobium phosphate catalysts are disclosed. Disadvantageously, some of these catalysts may also disintegrate in the presence of water.

U.S. Pat. No. 4,540,822 discloses a process for preparing predominantly linear polyethylenepolyamines from ethylenediamine and monoethanolamine employing a catalyst comprising a phosphorus compound deposited on a Group IVB metal oxide, such as titanium, zirconium and hafnium oxides. U.S. Pat. No. 4,578,518, U.S. Pat. No. 4,578,519, U.S. Pat. No. 4,584,406 and U.S. Pat. No. 4,588,842 teach along similar lines. Disadvantageously, phosphorus may leach out of these catalysts causing catalyst deactivation and reactor plugging.

It would be advantageous to have a process which eliminates the need for neutralizing hydrohalide salts and disposing of a waste salt stream. It would be more advantageous to have a process for the direct amination of aliphatic alcohols to polyalkylenepolyamines which also does not require expensive metals and large quantities of hydrogen. It would be even more advantageous if such a process produces a high selectivity for linearly-extended products and low selectivity for undesirable cyclic materials. It would be most advantageous if the catalyst for such a process is insoluble in the presence of amines and retains its physical integrity in the presence of water. In such a process the problems of catalyst leaching, reactor plugging, and catalyst separation would be avoided. Accordingly, the combined aforementioned advantages would render the amination process suitable for industrial applications.

SUMMARY OF THE INVENTION

This invention is a process of preparing linearly-extended polyalkylenepolyamines which comprises contacting a difunctional aliphatic alcohol with a reactant aliphatic amine in the presence of a catalytic amount of a catalyst, described hereinafter. The contacting is conducted under reaction conditions such that a mixture of polyalkylenepolyamines enriched in linearly-extended products is produced. For the purposes of this invention "linearly-extended products" are defined as amine products arising from the condensation of the difunctional aliphatic alcohol and the reactant amine with the elimination of by-product water. Linearly-extended products are to be distinguished from undesirable cyclic products, which arise when the condensation of the alcohol and amine reactants is followed by internal cyclization to form an undesirable nitrogen-containing heterocycle.

The catalyst employed in the process of this invention is a metal silicate wherein the metal is selected from the group consisting of Groups IIIB, IVB VB and the rare earth lanthanide metals. The Group IVB metal silicates are required to be essentially free of phosphorus, by which it is meant that the concentration of phosphorus is less than about 5 weight percent.

Advantageously, the process of this invention is direct, so that there is no need to neutralize a hydrohalide salt and eliminate a metal salt waste stream. More advantageously, the process of this invention does not require hydrogen. Even more advantageously, the process of this invention is capable of achieving high yields of valuable linearly-extended polyalkylenepolyamines and low yields of undesirable cyclic products. Most advantageously, the catalysts of this invention are insoluble in liquid amines and water: therefore, catalyst losses are minimized and the separation of products from the catalyst is relatively easy. Consequently, the combined advantages of the process of this invention make it suitable for industrial use.

The linearly-extended polyalkylenepolyamine products of this invention are useful as dispersants, surfactants, chelants, curing agents, and catalysts, and useful in the formation of urethane polymers, ureas, pesticides, and antihelminthic pharmaceutical products.

DETAILED DESCRIPTION OF THE INVENTION

The difunctional aliphatic alcohol which is employed in the process of this invention includes any aliphatic alcohol containing (a) at least one hydroxyl moiety bound to a primary carbon atom, and (b) at least one additional moiety selected from the group consisting of hydroxyl, primary amine and secondary amine functionalities. Examples of suitable difunctional alcohols include diols, such as ethylene glycol, propylene glycol, and 1,4-butanediol; triols such as glycerol, and higher polyols; polyether polyols such as diethylene glycol, dipropylene glycol, ethylene oxide-capped polypropylene glycol, and higher homologues of these compounds: alkanolamines such as ethanolamine, propanolamine and N-(2-aminoethyl)ethanolamine; polyether amino alcohols such as 2-($\beta$-aminoethoxy)ethanol: and hydroxyalkyl-substituted piperazines, such as N-(2-hydroxyethyl)piperazine, N,N'-bis(2-hydroxyethyl)piperazine, and N-(2-hydroxyethyl)bis-piperazinylethane. The difunctional alcohols are not limited to the aforementioned examples, and other equally suitable difunctional alcohols can be employed in the practice of this invention.

Preferably, the difunctional alcohols which are polyols, polyether amino alcohols, or alkanolamines are represented by the general formula:

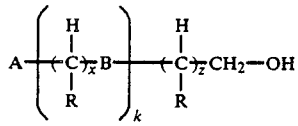

wherein A is OH or NHR; each B is independently NR or O; each R is independently hydrogen, an alkyl moiety of $C_1$–$C_{12}$ carbon atoms such as methyl, ethyl or propyl, a hydroxyalkyl or aminoalkyl moiety of $C_1$–$C_{12}$ carbon atoms, or a monocyclic aromatic moiety, such as phenyl, or tolyl, and further wherein R is attached to carbon, R is also hydroxyl or amino ($NH_2$); each x is independently an integer from 2 to about 12: k is an integer from 0 to about 150; and z is an integer from 1 to about 12. Preferably, each R is hydrogen. More preferably, each R is hydrogen, x is 2, and z is 1. Most preferably, each is hydrogen, A is $NH_2$, k is 0, z is 1, and the difunctional alcohol is monoethanolamine.

In those reactions wherein the difunctional alcohol contains a piperazine moiety, the preferred difunctional alcohols are represented by the general formula:

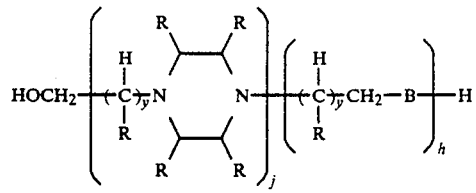

wherein each B is independently NR or O; each R is independently hydrogen, an alkyl moiety of $C_1$–$C_{12}$ carbon atoms such as methyl, ethyl or propyl, a hydroxyalkyl or aminoalkyl moiety of $C_1$–$C_{12}$ carbon atoms, or a monocyclic aromatic moiety, such as phenyl, or tolyl, and further wherein R is attached to carbon, R is also hydroxyl or amino ($NH_2$); each y is independently an integer from 0 to about 12; j is an integer from 1 to about 6; and h is an integer from 0 to about 6. Some examples of difunctional alcohols which satisfy this formula are N-(2-hydroxyethyl)piperazine, N-(2-hydroxyethyl)bispiperazine, N,N'-bis(2-hydroxyethyl)piperazine, and N,N'-bis(2-hydroxyethyl)bispiperazine. Preferably, each R is hydrogen. More preferably, each R is hydrogen, each y is independently 1 or 2, j is 1 or 2, h is 0, 1, or 2, and B is NR. Most preferably, each R is hydrogen, y is 1, j is 1, h is 0, and the compound is N-(2-hydroxyethyl)piperazine. For simplicity, the piperazine ring in the above-identified formula is shown with only one substituent (R) on the ring carbons. One skilled in the art will recognize that the other substituent on each ring carbon is hydrogen. Other reactant and product formulas containing piperazine rings and illustrated hereinbelow are drawn in the same manner.

The reactant amines which are employed in the process of this invention include ammonia and any primary or secondary aliphatic amine which is capable of animating the difunctional alcohol. Examples of suitable aliphatic amines include monoamines such as ethylamine, propylamine, butylamine, pentylamine, hexylamine, heptylamine, octylamine, diethylamine, dipropylamine, dibutylamine, dihexylamine, dicyolohexylamine, and dioctylamine; linear or branched alkylene diamines or polyamines such as ethylenediamine, propylenediamine, diethylenetriamine, triethylenetetramines, and tetraethylenepentamines; alkylene ether polyamines such as 2-($\beta$-aminoethoxy)ethylamine; piperazine, and mixtures of the above-identified amines. While the aforementioned amines are representative of those which are suitable in the process of this invention, other amines not recited herein may be equivalent and equally suitable.

Simple primary and secondary amines which are preferred for the process of this invention are represented by the general formula $R^1_2NH$, wherein each $R^1$ is independently hydrogen or a $C_1$–$C_{12}$ alkyl moiety. Preferably, the alkylenepolyamines and alkylene ether polyamines which are suitable in the process of this invention are represented by the general formula:

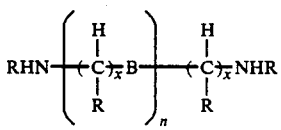

wherein each B is independently NR or O; each R is independently hydrogen, a $C_1$-$C_{12}$ alkyl moiety such as methyl or ethyl, a $C_1$-$C_{12}$ hydroxyalkyl or aminoalkyl moiety, or a monocyclic aromatic moiety such as phenyl or tolyl, and further wherein R is attached to carbon, R is also hydroxyl or amino: each x is independently an integer from 2 to about 12, and n is an integer from 0 to about 150. Preferably, each B is NR and the amine is an alkylenepolyamine. More preferably, the amine is an alkylenepolyamine and each R is hydrogen Even more preferably, each B is NR, each R is hydrogen, each x is 2, and the amine is an ethylenepolyamine. Most preferably, the amine is ethylenediamine.

In those reactions wherein the reactant amine contains a piperazine moiety, preferred piperazines or aminoalkyl-substituted piperazines are represented by the general formula:

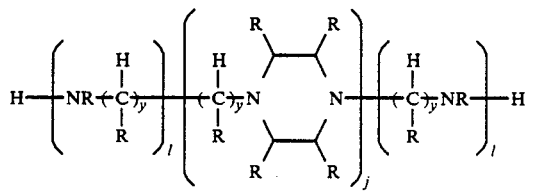

wherein each R is independently hydrogen, an alkyl moiety of $C_1$-$C_{12}$ carbon atoms such as methyl, ethyl or propyl, a hydroxyalkyl or aminoalkyl moiety of $C_1$-$C_{12}$ carbon atoms, or a monocyclic aromatic moiety, such as phenyl, or tolyl, and further wherein R is attached to carbon, R is also hydroxyl or amino: each y is independently an integer from 0 to about 12; each l is independently an integer from 0 to about 6; and j is an integer from 1 to about 6. Some examples of reactant amines which satisfy this formula include piperazine, N-(2-aminoethyl)piperazine, N,N'-bis(2-aminoethyl) piperazine, bis(piperazinyl)ethane, and N-(2-aminoethyl) bis-piperazinylethane. Preferably, each R is hydrogen More preferably, each R is hydrogen, y is 1 or 2, j is 1 or 2, and l is 0, 1, or 2. Most preferably, each R is hydrogen, y is 0, j is 1, and each l is 0, and the compound is piperazine.

In accordance with the process of this invention, any mole ratio of reactant amine to difunctional aliphatic alcohol can be used provided that the animation reaction proceeds to the desired linearly-extended polyalkylenepolyamine products. Typically, the alcohol is reacted with at least about one mole equivalent of reactant amine; however, an excess of reactant amine can be advantageously employed. Preferably, the mole ratio of reactant amine to difunctional alcohol is in the range from about 0.1 to about 20. More preferably, the mole ratio of reactant amine to difunctional alcohol is in the range from about 1 to about 15: most preferably from about 2 to about 10.

Although it is preferred to carry out the animation reaction in the absence of solvent, it is within the scope of the invention for a solvent to be used, if desired. Any solvent is acceptable provided that (1) it is not reactive with the difunctional alcohol and the reactant or product amines, and (2) it does not decompose under the conditions of the reaction. Some examples of suitable solvents include water, saturated aliphatic hydrocarbons such as pentane, hexane, heptane, octane, nonane, and decane, and aromatic hydrocarbons such as benzene, toluene, and xylene. The amount of solvent employed depends upon the particular reactants and reaction conditions. Any amount of solvent is acceptable that meets the intended purpose of use. If a solvent is used, typically the solvent constitutes from about 5 weight percent to about 95 weight percent of the feed stream. Preferably, the solvent constitutes from about 10 weight percent to about 80 weight percent of the feed stream.

The catalyst employed in the process of this invention is a metal silicate wherein the metal is selected from the group consisting of Groups IIIB, IVB and VB, and the rare earth lanthanide metals. Group IIIB metals include scandium, yttrium, lanthanum and actinium. Group IVB metals include titanium, zirconium and hafnium. Group VB metals include vanadium, niobium and tantalum. The lanthanum rare earth metals include cerium, praseodymium, neodymium, samarium, europium, gadolinium, terbium, dyprosium, holmium, erbium, thulium, ytterbium and lutetium. Preferably, the metal of the metal silicate catalyst is selected from the group consisting of scandium, yttrium, lanthanum, actinium, titanium, zirconium, hafnium, vanadium, niobium, tantalum, and cerium. More preferably, the metal of the metal silicate catalyst is selected from the group consisting of yttrium, lanthanum, titanium, zirconium, niobium, and cerium. Most preferably, the metal of the metal silicate catalyst is selected from the group consisting of yttrium, titanium, zirconium, and cerium. The metal silicate can be employed in an amorphous form containing a distribution of silicate anions of various sizes. Alternatively, the metal silicate can be employed in a crystalline form.

The Group IVB metal silicates are required to be essentially free of phosphorus. Preferably, the Groups IIIB, VB and lanthanide metal silicates are also essentially free of phosphorus. The term "essentially free," defined hereinbefore, means that each metal silicate contains less than about 5 weight percent phosphorus, preferably, less than about 2 weight percent phosphorus, more preferably, less than about 1 weight percent phosphorus Moreover, in preferred embodiments of the catalyst each of the aforementioned Groups IIIB, IVB, VB and lanthanide metal silicates is essentially free of aluminum. Likewise, the term "essentially free" means that each metal silicate contains less than about 5 weight percent aluminum. Preferably, each metal silicate contains less than about 2 weight percent aluminum, more preferably, less than about 1 weight percent aluminum.

The mole ratio of silicon to metal in the metal silicate catalyst will vary depending upon the metal cation, its valence, and the form of the silicate anion.

The common metal silicate catalysts which are employed in the process of this invention, such as titanium silicate and zirconium silicate, are commercially available. The less common silicates, such as yttrium silicate and cerium silicate, may be prepared by methods reported in *The Colloid Chemistry of Silica and Silicates* by Ralph K. Iler, Cornell University Press, 1955: or in *The Chemistry of Silica: Solubility, Polymerization, Colloid and Surface Properties, and Biochemistry*, by Ralph K.

Iler, John Wiley & Sons, 1979; and the references therein.

More specifically, the metal silicate catalyst can be prepared by any one of the following synthetic methods One, for example, comprises forming a mixture of silica ($SiO_2$) with the oxide of the desired metal and calcining at a temperature high enough to fuse the components, thereby forming the desired metal silicate. Another method, for example, involves the hydrolysis of mixtures of a tetra(alkoxy)silicon compound, such as tetra(ethoxy)silicon, and an alkoxide of the desired metal, such as, tetra(methoxy)titanium. The hydrolysis reaction yields the desired metal silicate.

Preferably, the metal silicate is prepared by direct precipitation from a mixture of two aqueous solutions, one of which contains a soluble silicate salt and the other of which contains a soluble salt of the desired metal. Typically, the soluble silicate salt is dissolved in a minimum amount of water which is heated, preferably to boiling, to aid in the dissolution of the salt. Optionally, the aqueous silicate solution is acidified with strong acid, such as nitric acid, in order to prepare larger silicate anions, such as $Si_2O_5^{2-}$ or $Si_3O_7^{2-}$ or higher polymeric anions. Similarly, a soluble metal salt containing the desired metal ion is dissolved in a minimum amount of hot water to make a second solution. The soluble metal salt can be, for example, a metal nitrate, such as lanthanum nitrate or titanium nitrate or niobium nitrate; or a metal chloride, such as yttrium chloride, titanium chloride, niobium chloride or cerium chloride. The two solutions are mixed yielding a precipitate of the desired metal silicate catalyst. The catalyst is filtered and dried by methods well-known in the art.

The metal silicate catalyst can be soluble in the animation reaction mixture, and therefore, can act as a homogeneous catalyst Alternatively, the metal silicate catalyst can be insoluble in the reaction mixture, and therefore, can act as a heterogeneous catalyst. The solubility of the catalyst varies depending upon the specific alcohol and amine reactants, the size of the silicate anion, and the specific metal cation associated with the silicate anion. Preferably, the silicate catalyst is insoluble and acts as a heterogeneous catalyst, because then it is easier to separate the catalyst from the product stream.

The metal silicate catalyst can be made more insoluble by applying it to a support material. Any support material is acceptable provided that it does not enhance the formation of undesirable cyclic products in the process of this invention. Suitable supports include carbon and any refractory oxide such as zirconia, boria, thoria, magnesia, titania, tantala, chromia, silica, kielselguhr, zeolites, and mixtures thereof. Preferably, the support material is titania or silica, more preferably, silica. The support material typically has a surface area of at least about 0.1 $m^2/g$. Preferably, the support material has a surface area in the range from about 5 $m^2/g$ to about 600 $m^2/g$: and most preferably in the range from about 50 $m^2/g$ to about 200 $m^2/g$. These surface areas are measured by the Brunauer-Emmett-Teller BET) method. The BET method is described by R. B. Anderson, in *Experimental Methods in Catalytic Research*, Academic Press, 1968, pp. 48–66.

The catalyst can be applied to the support material in any known fashion, such as the impregnation technique, or by precipitation in situ from the catalyst preparation reaction. Alternatively, the catalyst can be mixed with the support material, and the mixture can be heated to promote dehydration. The dehydrated composition generally comprises a catalyst which is strongly bound to the support material This is particularly useful when the catalyst is soluble in the reaction mixture and it is necessary to enhance its insolubility. Typically, from about 0.5 weight percent to about 30 weight percent metal silicate is placed on the support.

Preferably, the catalyst or the supported catalyst composition is calcined prior to use. Generally, the calcination is conducted in air at a temperature not greater than about 1000° C. More preferably, the calcination is conducted at a temperature in the range from about 200° C. to about 800° C., most preferably, in the range from about 250° C. to about 550° C.

The amount of catalyst which is employed in the process of this invention is any amount which is effective in producing the desired linearly-extended polyalkylenepolyamine products. The amount of catalyst varies considerably depending upon the specific reactants and reaction conditions employed. Typically, in a batch reactor the amount of catalyst is in the range from about 0.1 weight percent to about 20 weight percent based on the weight of reactant amine. Preferably, the amount of catalyst is in the range from about 1 weight percent to about 15 weight percent based on the weight of reactant amine.

The process of this invention can be carried out in any suitable reactor, including batch reactors, continuous fixed-bed reactors, slurry reactors, fluidized bed reactors, and catalytic distillation reactors. Preferably, the reactor is a continuous fixed-bed reactor.

The difunctional aliphatic alcohol and the aliphatic amine reactants are contacted with the catalyst at any operable temperature which promotes the animation process of this invention and yields the desired linearly-extended polyalkylenepolyamine products. Typically, the temperature is in the range from about 200° C. to about 350° C. Preferably, the temperature is in the range from about 240° C. to about 325° C. More preferably, the temperature is in the range from about 260° C. to about 315° C. Below the preferred lower temperature the conversion of difunctional alcohol may be low. Above the preferred upper temperature the selectivity for linearly-extended polyalkylenepolyamines may decrease.

Likewise, the reactants are contacted with the catalyst at any operable pressure which promotes the animation process of this invention and yields the desired linearly-extended polyalkylenepolyamine products. Typically, the pressure is sufficient to maintain the reactants in the liquid state at the temperature of the reaction. Preferably, the pressure is in the range from about atmospheric to about 4000 psig. More preferably, the pressure is in the range from about 100 psig to about 3000 psig. Most preferably, the pressure is in the range from about 400 psig to about 2000 psig. In batch reactors the pressure is autogenous, and depends on the vapor pressures of the reactants and products, and upon the temperature of the reaction.

When the process of this invention is conducted in a continuous flow reactor, the flow rate of the reactants can be varied. Generally, the difunctional alcohol and the reactant amine are premixed to form a feed stream, which is fed into the reactor at any operable flow rate which yields predominantly linearly-extended polyalkylenepolyamine products. The flow rate is expressed as the liquid hourly space velocity (LHSV) and is given in units of grams of total reactants per milliliter of total reactor volume per hour, g ml$^{-1}$ hr$^{-1}$. Preferably, the liquid hourly space velocity is in the range from about 0.1 g ml$^{-1}$ hr$^{-1}$ to about 10.0 g ml$^{-1}$ hr$^{-1}$ more preferably in the range from about 0.5 g ml$^{-1}$ hr$^{-1}$ to about 4.0 g ml$^{-1}$ hr$^{-1}$ It is understood that the space velocity controls the residence time of the reactants in the continuous flow reactor.

When the process of this invention is conducted in a batch reactor, the reaction time determines the length of contact between the reactants and the catalyst. Any reaction time is acceptable which allows for the amination reaction to proceed to the desired linearly-extended polyalkylenepolyamine products. The reaction time depends on the quantity of reactants, the quantity of catalyst, the temperature of the reaction and desired degree of conversion. Preferably, the reaction time in a batch reactor is in the range from about 1 hour to about 20 hours.

When the difunctional aliphatic alcohol and the reactant amine are contacted in accordance with the process of this invention, a reaction occurs to form a polyalkylenepolyamine product. Specifically, the hydroxyl moiety of the difunctional alcohol reacts with the reactant amine to form the polyalkylenepolyamine, and water is eliminated as a by-product. If the difunctional alcohol contains two or more hydroxyl moieties, the reactant amine may react at each hydroxyl. Preferably, the product is a mixture of polyalkylenepolyamines enriched in linearly-extended products, such as straight-chain or branched-chain adducts. For example, if the reactants are monoethanolamine and ethylenediamine, the polyalkylenepolyamine products are preferably diethylenetriamine and straight-chain and branched triethylenetetramines. Similarly, if the reactants are ethylene glycol and piperazine, the preferred product is N-(2-hydroxyethyl)piperazine, which is an alcohol-extended piperazine. If the reactants are monoethanolamine and piperazine, the preferred product is N-(2-aminoethylpiperazine), which is an amine-extended piperazine. In addition to linearly-extended products, certain undesirable cyclic by-products may be formed in lesser amounts. With piperazine-containing reactants the internally cyclized product 1,4-diaza-2.2.2]-bicyclooctane is an example of such an undesirable cyclic product. With linear alkyleneamine or alkanolamine reactants which do not contain piperazine rings, then piperazine itself is an example of such an undesirable cyclic product.

The preferred linearly-extended polyalkylenepolyamines which do not contain a piperazine moiety can be represented by the general formula:

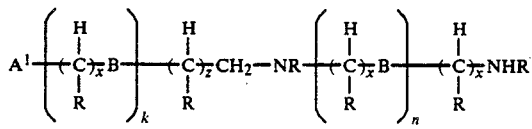

wherein each B is independently NR or O; each R is independently hydrogen, an alkyl moiety of $C_1-C_{12}$ carbon atoms such as methyl, ethyl or propyl, a hydroxyalkyl or aminoalkyl moiety of $C_1-C_{12}$ carbon atoms, or a monocyclic aromatic moiety, such as phenyl, or tolyl, and further wherein R is attached to carbon, R is also hydroxyl or amino: each x is independently an integer from 2 to about 12; each n and k is independently an integer from 0 to about 150: and z is an integer from 1 to about 12: wherein A1 is OH, NHR or:

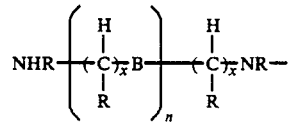

Preferably, each R is hydrogen. More preferably, each R is hydrogen, $A^1$ is $NH_2$, k is 0, y is 2, and z is 1. Most preferably, each R is hydrogen, $A^1$ is $NH_2$, k is 0, y is 2, z is 1, and n is 1, 2, or 3: thus, the polyalkylenepolyamines are diethylenetriamine, triethylenetetramine, and tetraethylenepentamine.

The preferred alcohol-extended and amine-extended piperazine products can be represented by the general formula:

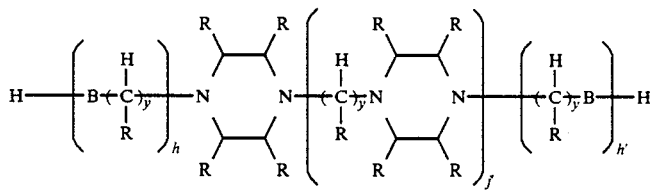

wherein each B is independently O or NR; each R is independently hydrogen, an alkyl moiety of $C_1-C_{12}$ carbon atoms such as methyl, ethyl or propyl, a hydroxyalkyl or aminoalkyl moiety of $C_1-C_{12}$ carbon atoms, or a monocyclic aromatic moiety, such as phenyl, or tolyl, and further wherein when R is attached to carbon, R is also hydroxyl or amino: each y is independently an integer from 0 to about 12; h and h' are each independently integers from 0 to about 6; and j' is an integer from 0 to about 6. Some examples of products which satisfy this formula include N-(2-aminoethyl) piperazine, N-(2-hydroxyethyl)piperazine, 1,2-bis(-piperazinyl)ethane (i.e. bispiperazine) and higher oligomers of piperazine. Preferably, each R is hydrogen. More preferably, each R is hydrogen, y is 1 or 2, j' is 1 or 2, h and h' are each independently 0-2, and each B is NR. Most preferably, each B is NR, each R is hydrogen, y is 2, h is 1, j' and h' are each 0, and the product is N-(2-aminoethyl)piperazine.

For the purposes of this invention, "conversion" is defined as the weight percentage of difunctional aliphatic alcohol lost from the feed stream as a result of reaction. The conversion can vary widely depending upon the reactants, the form of the catalyst, and the process conditions such as temperature, pressure, and flow rate. Within the preferred temperature range, as the temperature increases the conversion generally increases. Within the preferred space velocity range, as the space velocity increases the conversion generally decreases. Typically, the conversion of the difunctional alcohol is at least about 15 weight percent. Preferably, the conversion is at least about 20 weight percent, more preferably at least about 30 weight percent, most preferably at least about 40 weight percent.

Likewise, for the purposes of this invention "selectivity" is defined as the weight percentage of converted difunctional alcohol which forms a particular polyalkylenepolyamine product. Typically, the selectivities also vary widely depending upon the reactants, the form of the catalyst, and the process conditions. Typically, the process of this invention achieves high selectivities to linearly-extended polyalkylenepolyamines. Within the preferred temperature range, as the temperature increases the selectivity for linearly-extended polyalkylenepolyamines generally decreases. Within the preferred space velocity range, as the space velocity increases the selectivity for linearly-extended polyalkylenepolyamines generally increases. Preferably, the combined selectivity to all linearly-extended polyalkylenepolyamines is at least about 50 weight percent: more preferably, at least about 60 weight percent; most preferably, at least about 70 weight percent.

Where applicable, the efficiency of the animation reaction in forming linearly-extended polyalkylenepolyamines is measured by the weight ratio of diethylenetriamine to piperazine, abbreviated DETA/-PIP. The higher the value of this ratio, the more linearly-extended polyamines are present in the product mixture. Preferably, the DETA/PIP weight ratio is at least about 2. More preferably, the DETA/PIP weight ratio is at least about 5: most preferably, at least about 10. Another measure of the efficiency of forming linearly-extended products is the weight percentage of triethylenetetramines which are non-cyclic, % NC TETA. Preferably, % NC TETA is at least about 50 weight percent. More preferably, the %NC TETA is at least about 70 weight percent; most preferably, at least about 80 weight percent.

ILLUSTRATIVE EMBODIMENTS

The following examples illustrate the invention, but are not intended to be limiting thereof. All percentages are given as weight percent, unless noted otherwise. In some instances the following abbreviations are used to indicate the reactants and products:

MEA—monoethanolamine
EG—ethylene glycol
EDA—ethylenediamine
DETA—diethylenetriamine
TETA—triethylenetetramine
TEPA—tetraethylenepentamine
PEHA—pentaethylenehexamine
PIP—piperazine
AEEA—N-(2-aminoethyl)ethanolamine
AEP—N-(2-aminoethyl)piperazine
DIAEP—N,N'-bis(2-aminoethyl)piperazine
PEEDA—(piperazinylethyl)ethylenediamine
BISPIP—1,2-bis(piperazinyl)ethane or bispiperazine
DABCO—1,4-diaza-2.2.2]-bicyclooctane
AEPEEDA—N-(aminoethylpiperazinylethyl) ethylenediamine
PEDETA—(piperazinylethyl)diethylenetriamine
AEBISPIP—N-(2-aminoethyl)bispiperazine
PEAEP—(piperazinylethyl)aminoethylpiperazine
TRISPIP—N,N'-bis(2-piperazinylethyl) piperazine or trispiperazine

EXAMPLES 1-6

(a) Preparation of Catalysts

A series of metal silicate catalysts is prepared according to the following general procedure: $Na_2SiO_3.9H_2O$ is dissolved in 1200 ml of water and heated to 80° C. Concentrated nitric acid is slowly added to the solution so that no precipitate forms during the addition. The acidified silicate solution is heated to boiling and the volume is raised to 2000 ml with water. In a separate flask a metal nitrate or metal chloride salt is dissolved in 2000 ml of water and heated to boiling. The acidified silicate solution is added hot at a rate of 100 ml/min to the nitrate solution with rapid stirring. A precipitate forms. The supernatent and the precipitate are heated and stirred for about 3 hours at boiling, then cooled overnight at room temperature. The cooled mixture is filtered, and the precipitate is washed with about 2000 ml of water and refiltered. The washing procedure is repeated twice more, and the resulting filtercake is dried at 100° C. overnight. The dried filtercake is calcined under air at 300° C. or 550° C. over a second night to yield a metal silicate catalyst, which is employed in the reforming process of this invention. Table I lists the kind and quantity of metal salts used in preparing the nitrate or chloride solutions, the quantities of nitric acid and sodium silicate used in making the sodium silicate solution, and the approximate formula of the resulting metal silicate catalyst.

TABLE I

| EX. | Metal Salt (g) | $Na_2SiO_3.9H_2O$ (g) | $HNO_3$ (ml) | Approx. Formula |
|---|---|---|---|---|
| 1a | $YCl_3.6H_2O$ (53.4) | 150.4 | 33 | $Y_2(Si_2O_5)_3$ |
| 2a | $La(NO_3)_3.6H_2O$ (108.3) | 213.2 | 48.5 | $La_2(Si_2O_5)_3$ |
| 3a | $(NH_4)_2Ce(NO_3)_6$ (183.6) | 571.7 | 131 | $Ce(Si_3O_7)_2$ |
| 4a | $ZrOCl_2.4H_2O$ (100.1) | 228.0 | 50.0 | $ZrO(Si_2O_5)$ |
| 5a | $NbCl_5$ (76.0) | 200.0 | 0.0 | $Nb_2O_5.5SiO_2$ |

(b) Animation of Monoethanolamine with Piperazine

Monoethanolamine, piperazine and a silicate catalyst, prepared hereinabove or obtained commercially, are placed in a batch reactor equipped with a pressure gauge and a temperature sensor. The reactor is sealed, flushed with nitrogen, heated to 300° C., and maintained thereat for 5 hours. At the end of the reaction period the reactor is cooled to room temperature and the liquid phase contents are analyzed by gas phase chromatography. The quantities of reactants, process conditions and results are found in Table II.

TABLE II

| EX.① | PIP (g) | MEA (g) | % MEA Conv. per g catalyst | % Selectivity | | | | | | | | |
|---|---|---|---|---|---|---|---|---|---|---|---|---|
| | | | | DABCO | AEP | DIAEP | PEEDA | BISPIP | AEPEEDA | PEDETA | AEBISPIP | PEAEP |
| 1b | 29.0 | 20.6 | 40.7 | 5.1 | 73.7 | 4.3 | 9.3 | 5.1 | — | — | 1.5 | 1.0 |
| 2b | 28.9 | 21.0 | 19.6 | 7.6 | 73.7 | 2.9 | 9.7 | 6.1 | — | — | — | — |

TABLE II-continued

| EX.[1] | PIP (g) | MEA (g) | % MEA Conv. per g catalyst | % Selectivity | | | | | | | | |
|---|---|---|---|---|---|---|---|---|---|---|---|---|
| | | | | DABCO | AEP | DIAEP | PEEDA | BISPIP | AEPEEDA | PEDETA | AEBISPIP | PEAEP |
| 3b | 29.0 | 20.6 | 27.0 | 1.4 | 84.9 | 1.6 | 5.8 | 6.3 | — | — | — | — |
| 4b | 29.3 | 20.9 | 41.2 | 3.0 | 68.4 | 5.2 | 9.1 | 7.6 | — | — | 2.8 | 1.6 |
| 5b | 28.9 | 20.3 | 39.3 | 3.9 | 79.3 | 3.6 | 9.8 | 2.6 | — | — | 0.8 | — |
| 6[2] | 28.6 | 21.5 | 43.7 | 1.0 | 76.0 | 6.1 | 9.0 | 4.6 | 0.6 | — | 1.7 | 1.0 |

[1]Catalysts of Examples 1, 3 and 6 calcined at 550° C.; Cataylsts of Examples 2, 4 and 5 calcined at 300° C. Amount of catalyst employed in each example, 1.0 g.
[2]Catalyst of Example 6 is a commercial sample of titanium silicate TiO$_2$.3SiO$_2$, 30.7 weight percent TiO$_2$.

It is seen that metal silicates of Groups IIIB, IVB, VB and the lanthanide metals catalyze the reaction of monoethanolamine and piperazine to a mixture of predominantly aminoethylpiperazine and other linearly-extended piperazines.

EXAMPLE 7

The niobium silicate catalyst (1 g) of Example 5a is employed in the reaction of monoethanolamine (22.8 g) with ethylenediamine (46.1 g) in an EDA/MEA mole ratio of 2/1 at 300° C. for 10 hr according to the procedure described in Examples 1-6 hereinabove with the following results: Conversion of MEA, 22.5 percent; Selectivity to DETA, 38.6; PIP, 12.6; DABCO, 1.1; AEEA, 14.8: AEP, 6.3: AEDETA, 0.6: TETA, 4.6: DIAEP, 0.6; PEEDA, 0.6; unknown #1, 5.7: and unknown #2, 14.2 weight percent. The DETA/PIP ratio is 2.7; and the percentage of TETA's which are non-cyclic is 79.2. It is seen that niobium silicate catalyzes the reaction of monoethanolamine with ethylenediamine to predominantly linearly-extended polyethylenepolyamines.

What is claimed is:

1. A process of preparing linearly-extended polyalkylenepolyamines comprising contacting a difunctional aliphatic alcohol, characterized as having (a) at least one hydroxyl moiety bound to a primary carbon atom, and (b) at least one additional moiety selected from the group consisting of hydroxyl, primary amine and secondary amine functionalities, with ammonia or any primary or secondary aliphatic amine which is capable of animating the difunctional alcohol, the contacting occurring in the presence of a catalytic amount of a metal silicate wherein the metal is selected from the group consisting of Groups IIIB, IVB, VB and the lanthanide metals with the proviso that the Group IVB metal silicate is essentially free of phosphorus, the contacting occurring under reaction conditions such that a mixture of polyalkylenepolyamines enriched in linearly-extended products is produced.

2. The process of claim 1 wherein the difunctional alcohol is represented by the formula:

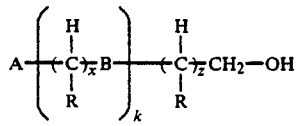

wherein A is OH or NHR; each B is independently NR or O; each R is independently hydrogen, an alkyl moiety of C$_1$-C$_{12}$ carbon atoms, a hydroxyalkyl or aminoalkyl moiety of C$_1$-C$_{12}$ carbon atoms, or a phenyl or tolyl moiety, and further wherein R is attached to carbon, R is also hydroxyl or amino: x is an integer from 2 to about 12: k is an integer from 0 to about 150: and z is an integer from 1 to about 12.

3. The process of claim 2 wherein each R is hydrogen.

4. The process of claim 3 wherein x is 2 and z is 1.

5. The process of claim 4 wherein each R is hydrogen, A is NH$_2$, k is 0, z is 1, and the difunctional aliphatic alcohol is monoethanolamine.

6. The process of claim 1 wherein the difunctional alcohol is represented by the following formula:

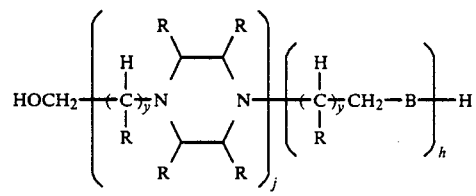

wherein each B is independently NR or 0; each R is independently hydrogen, an alkyl moiety of C$_1$-C$_{12}$ carbon atoms, a hydroxyalkyl or aminoalkyl moiety of C$_1$-C$_{12}$ carbon atoms, or a phenyl or tolyl moiety, and further wherein R is attached to carbon, R is also hydroxyl or amino: each y is independently an integer from 0 to about 12; j is an integer from 1 to about 6: and h is an integer from 0 to about 6.

7. The process of claim 6 wherein the difunctional alcohol is N-(2-hydroxyethyl)piperazine.

8. The process of claim 1 wherein the reactant amine is represented by the formula:

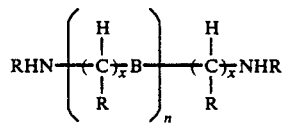

wherein each B is independently NR or 0: each R is independently hydrogen, an alkyl moiety of C$_1$-C$_{12}$ carbon atoms, a hydroxyalkyl or aminoalkyl moiety of C$_1$-C$_{12}$ carbon atoms, or a phenyl or tolyl moiety, and further wherein R is attached to carbon, R is also hydroxyl or amino; each x is independently an integer from 2 to about 12, and n is an integer from 0 to about 150.

9. The process of claim 8 wherein each B is NR.

10. The process of claim 9 wherein the amine is an ethylenepolyamine.

11. The process of claim 1 wherein the reactant amine is represented by the formula:

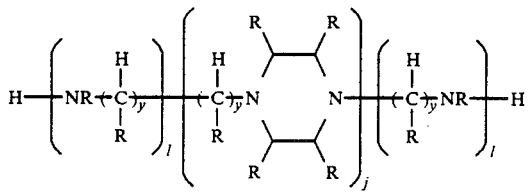

wherein each R is independently hydrogen, an alkyl moiety of $C_1$–$C_{12}$ carbon atoms, a hydroxyalkyl or aminoalkyl moiety of $C_1$–$C_{12}$ carbon atoms, or a phenyl or tolyl moiety, and further wherein R is attached to carbon, R is also hydroxyl or amino; each y is independently an integer from 0 to about 12; each l is independently an integer from 0 to about 6: and j is an integer from 1 to about 6.

12. The process of claim 11 wherein each R is hydrogen, y is 0, j is 1, and each l is 0, and the reactant amine is piperazine.

13. The process of claim 1 wherein the mole ratio of reactant amine to difunctional aliphatic alcohol is at least about 1.

14. The process of claim 1 wherein the metal silicate catalyst is essentially free of aluminum.

15. The process of claim 14 wherein the aluminum concentration of the metal silicate is less than about 1 weight percent.

16. The process of claim 1 wherein the phosphorus concentration of the Group IVB metal silicate is less than about 1 weight percent.

17. The process of claim 1 wherein the metal of the metal silicate is selected from the group consisting of scandium, yttrium, lanthanum, actinium, titanium, zirconium, hafnium, vanadium, niobium, tantalum, and cerium.

18. The process of claim 17 wherein the metal of the metal silicate is selected from the group consisting of yttrium, lanthanum, titanium, zirconium, niobium, and cerium.

19. The process of claim 18 wherein the metal silicate is yttrium silicate.

20. The process of claim 18 wherein the metal silicate is zirconium silicate.

21. The process of claim 1 wherein the amount of catalyst is in the range from about 0.1 weight percent to about 20 weight percent based on the weight of reactant amine.

22. The process of claim 1 wherein the temperature is in the range from about 200° C. to about 350° C.

23. The process of claim 1 wherein the pressure is in the range from about atmospheric to about 4000 psig.

24. The process of claim 1 wherein the liquid hourly space velocity is in the range from about 0.1 g ml$^{-1}$ hr$^{-1}$ to about 10.0 g ml$^{-1}$ hr$^{-1}$.

25. The process of claim 1 wherein the linearly-extended polyalkylenepolyamines are represented by the formula:

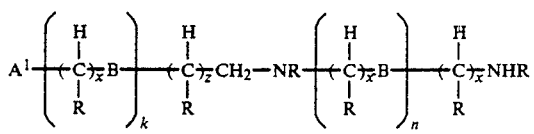

wherein each B is independently NR or O, each R is independently hydrogen, an alkyl moiety of $C_1$–$C_{12}$ carbon atoms, a hydroxyalkyl or aminoalkyl moiety of $C_1$–$C_{12}$ carbon atoms, or a phenyl or tolyl moiety, and further wherein R is attached to carbon, R is also hydroxyl or amino; each x is independently an integer from 2 to about 12: z is an integer from 1 to about 12: k and n are each integers from 1 to about 150; and wherein $A^1$ is OH, NHR or:

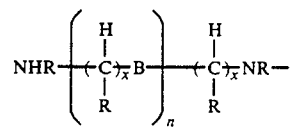

26. The process of claim 25 wherein each R is hydrogen.

27. The process of claim 26 wherein $A^1$ is $NH_2$, k is 0, y is 2, and z is 1.

28. The process of claim 1 wherein the polyalkylenepolyamine product is an alcohol-extended or amine-extended piperazino which is represented by the general formula:

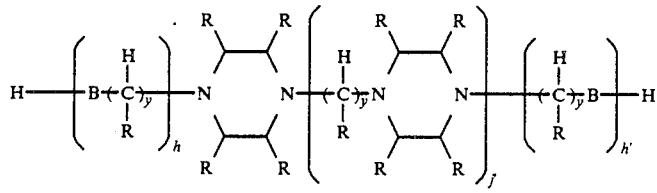

wherein each B is independently O or NR; each R is independently hydrogen, an alkyl moiety of $C_1$–$C_{12}$ carbon atoms, a hydroxyalkyl or aminoalkyl moiety of $C_1$–$C_{12}$ carbon atoms, and further wherein R is attached to carbon, R is also hydroxyl or amino; each y is independently an integer from 0 to about 12; h and h' are each independently integers from 0 to about 6; and j' is 1 or 2.

29. The process of claim 1 wherein the polyalkylenepolyamine product is an amine-extended piperazine which is represented by the general formula:

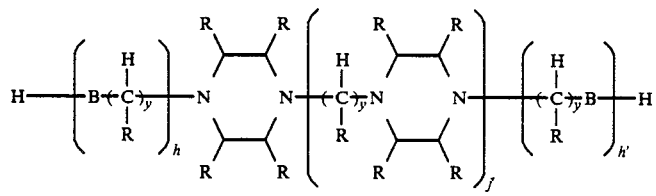

wherein each B is NR; each R is hydrogen, each y is 2, h is 1, j' and h' are each 0, and the compound is N-(2-aminoethyl)piperazine.

30. A process of preparing non-cyclic polyethylene polyamines comprising contacting monoethanolamine with ethylenediamine in the presence of a catalytic amount of niobium silicate, the contacting occurring at a temperature in the range from about 200° C. to about 350° C., a pressure in the range from about 100 psig to about 3000 psig, and a liquid hourly space velocity in the range from about 0 1 g ml$^{-1}$ hr$^{-1}$ to about 10.0 g ml$^{-1}$ hr$^{-1}$ such that a mixture of polyethylenepolyamines enriched in linearly-extended products is formed.

31. The process of claim 30 wherein the DETA/PIP mole ratio is at least about 2.

32. The process of claim 30 wherein the percentage of triethylenetetramines which is non-cyclic is at least about 70 weight percent.

33. A process of preparing alcohol-extended and/or amine-extended piperazines comprising contacting monoethanolamine with piperazine in the presence of a catalytic amount of a metal silicate selected from the group consisting of Group IIIB, IVB, VB and the lanthanide metal silicates with the proviso that the Group IVB metal silicate is essentially free of phosphorus, the contacting occurring at a temperature in the range from about 200° C. to about 350° C., a pressure in the range from about 100 psig to about 3000 psig, and a liquid hourly space velocity in the range from about 0.1 g ml$^{-1}$ hr$^{-1}$ to about 10.0 g ml$^{-1}$ hr$^{-1}$ such that a mixture of alcohol-extended and/or amine-extended piperazines is formed.

34. The process of claim 33 wherein the metal silicate is yttrium, zirconium, titanium or cerium silicate.

* * * * *

UNITED STATES PATENT AND TRADEMARK OFFICE
CERTIFICATE OF CORRECTION

PATENT NO. : 5,073,635

DATED : December 17, 1991

INVENTOR(S) : Robert G. Bowman; David C. Molzahn; and George E. Hartwell, all of Midland, Michigan.

It is certified that error appears in the above-identified patent and that said Letters Patent is hereby corrected as shown below:

Column 13, line 68, delete " amino: " and insert -- amino; --.

Column 14, line 17, delete " 12: " and insert -- 12; --.

Column 14, line 17, delete " 150: " and insert -- 150; --.

Column 14, line 42, delete " amino: " and insert -- amino; --.

Column 14, line 43, delete " 6: " and insert -- 6; --.

Column 14, line 56, delete " 0: " and insert -- 0; --.

Column 15, line 17, delete " 6: " and insert -- 6; --.

UNITED STATES PATENT AND TRADEMARK OFFICE
CERTIFICATE OF CORRECTION

PATENT NO. : 5,073,635

DATED : December 17, 1991

INVENTOR(S) : Robert G. Bowman; David C. Molzhan; and George E. Hartwell, all of Midland, Michigan.

It is certified that error appears in the above-identified patent and that said Letters Patent is hereby corrected as shown below:

Column 16, line 23, should read -- from 2 to about 12; z is an integer from 1 to about 12; k --.

Column 16, line 39, delete " piperazino " and insert -- piperazine --.

Column 17, line 26, delete " about 0 1 " and insert -- about 0.1 --.

Signed and Sealed this

Fourth Day of May, 1993

*Attest:*

MICHAEL K. KIRK

*Attesting Officer*  Acting Commissioner of Patents and Trademarks